Figure 1A:
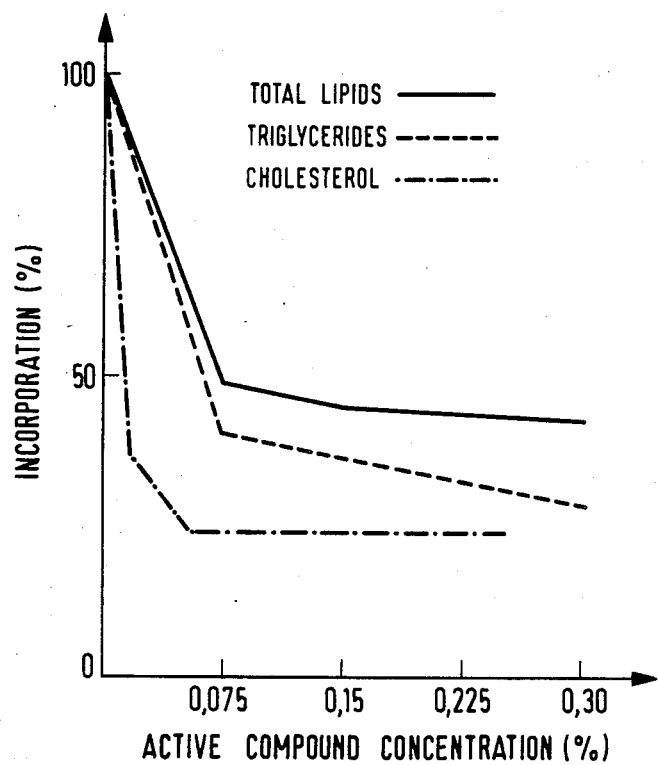

United States Patent [19]

Bar-Tana

[11] Patent Number: 4,689,344

[45] Date of Patent: Aug. 25, 1987

[54] LONG-CHAIN α,ω-DICARBOXYLIC ACIDS AND DERIVATIVES THEREOF AND PHARMACEUTICAL COMPOSITIONS CONTAINING THEM

[75] Inventor: Jacob Bar-Tana, Jerusalem, Israel

[73] Assignee: Epis S.A., Zug, Switzerland

[21] Appl. No.: 623,673

[22] Filed: Jun. 22, 1984

Related U.S. Application Data

[63] Continuation-in-part of Ser. No. 443,315, Nov. 22, 1982, abandoned.

[30] Foreign Application Priority Data

Dec. 15, 1981 [IL] Israel ........................................ 64542

[51] Int. Cl.⁴ ..................... A61K 31/16; A61K 31/20; A61K 31/225; A61K 31/275
[52] U.S. Cl. .................... 514/527; 514/519; 514/528; 514/529; 514/533; 514/547; 514/558; 514/559; 514/560; 514/616; 514/623; 514/624; 514/625; 514/626; 514/627; 514/628; 560/81; 560/82; 560/127; 560/154; 560/171; 560/190; 560/192; 260/546; 558/439; 558/442; 562/459; 562/468; 562/488; 562/489; 562/498; 562/506; 562/509; 562/565; 562/571; 562/582; 562/590; 562/594; 562/595; 562/596
[58] Field of Search ................ 560/190, 192; 562/590, 562/596; 260/465.4; 514/558, 527, 547, 616, 528, 560, 625

[56] References Cited

U.S. PATENT DOCUMENTS

| | | | |
|---|---|---|---|
| 2,971,915 | 2/1961 | Borsoff et al. .................. | 562/590 X |
| 3,678,102 | 7/1972 | Isard et al. ...................... | 560/190 X |
| 3,773,946 | 11/1973 | Creger ............................. | 424/318 |
| 3,776,951 | 12/1973 | Failey et al. ..................... | 562/590 |
| 3,930,024 | 12/1975 | Creger ............................ | 424/309 X |

OTHER PUBLICATIONS

Schisla; et al; J. Org. Chem., 35 (1970), pp. 3224–3230.
Beilstein; vol. 2; 2nd Supp., (1942), p. 627; Springes–Verlag, Berlin.
Beilstein; vol. 2; 4th Supp., (1976), pp. 2168, 2169, 2174, 2180, 2181, 2191, 2192, Springes–Verlag, Berlin.
Bouvier, et al.; Bull. Soc. Chim. Fr. (1975), No. 9–10, pp. 2195–2201.

Primary Examiner—Joseph Paul Brust
Attorney, Agent, or Firm—Browdy and Neimark

[57] ABSTRACT

A novel class of compounds has been found to be effective in blocking cholesterol and neutral lipid synthesis in-vivo without adversely affecting energy metabolism, useful for the treatment of obesity, hyperlipidemia and maturity-onset diabetes. The active compounds have the general formula

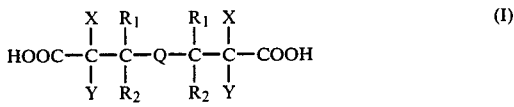

(I)

or in-vivo hydrolyzable functional derivatives of the carboxylic groups thereof, wherein $R_1$ and $R_2$ each independently represents an unsubstituted or substituted hydrocarbyl or hetercyclyl radical;

X and Y each independently represents hydrogen, optionally substituted lower alkyl, halogen, cyano, carboxy, lower alkoxycarbonyl or carbamoyl; and Q represents a diradical consisting of a linear chain of 8 to 14 carbon atoms, one or more of which may be replaced by heteroatoms, said chain being optionally substituted by inert substituents and one or more of said carbon or heteratom chain members optionally forming part of a ring structure.

19 Claims, 8 Drawing Figures

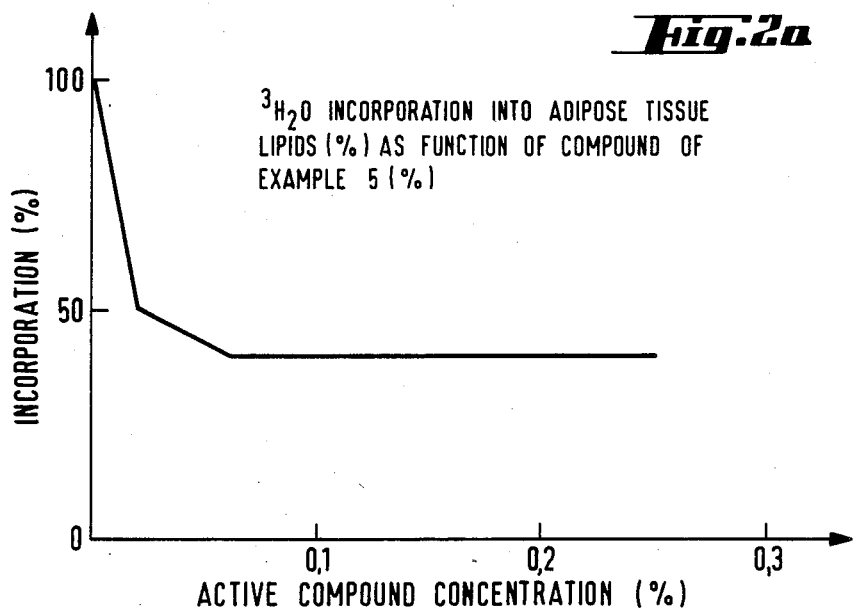
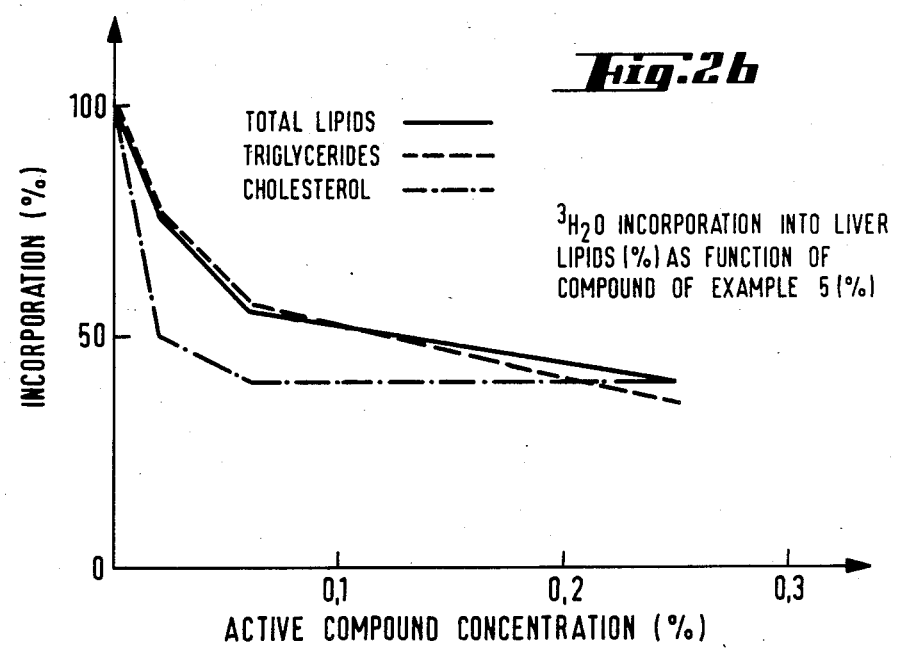

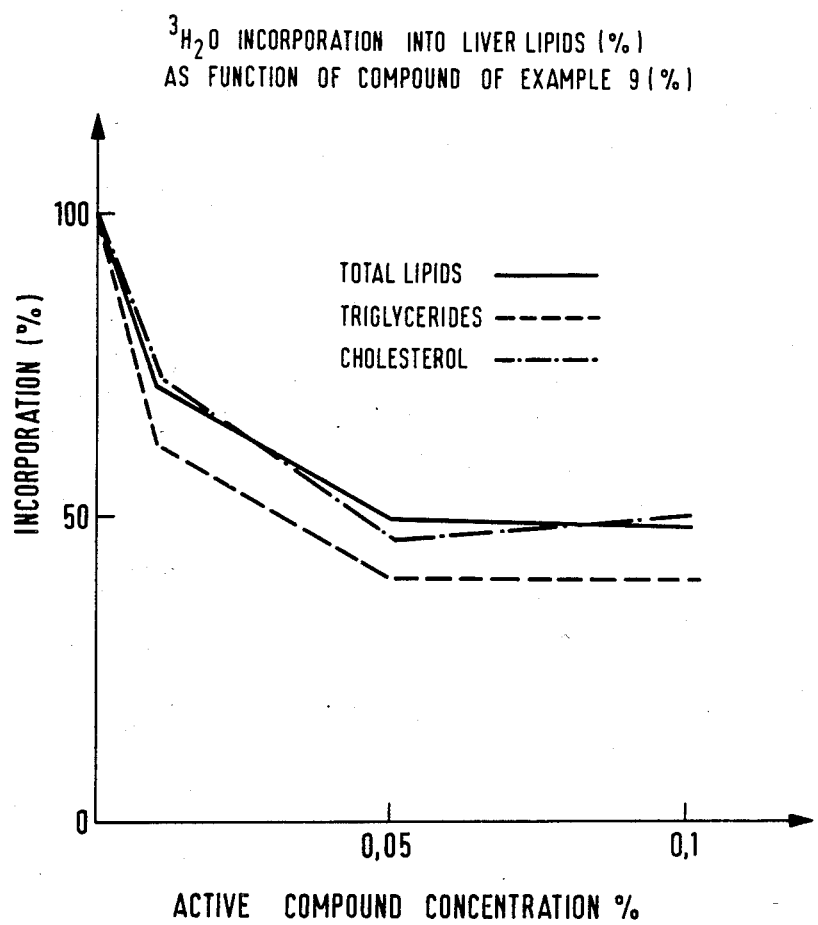

I PRETREATMENT
II 27th D. OF TREATMENT (0,1%) OF COMPOUND OF EXAMPLE 4
III 71th D. OF TREATMENT (0,1%) OF COMPOUND OF EXAMPLE 4
IV 34th D. AFTER TREATMENT ELIMINATION
V 53th D. AFTER TREATMENT ELIMINATION

LONG-CHAIN α,ω-DICARBOXYLIC ACIDS AND DERIVATIVES THEREOF AND PHARMACEUTICAL COMPOSITIONS CONTAINING THEM

This is a continuation in part of copending application Ser. No. 443,315 filed Nov. 22, 1982, now withdrawn without prejudice in favor of copending application Ser. No. 769,765, now U.S. Pat. No. 4,634,795, issued 1-6-87.

The present invention concerns novel derivatives of long-chain α,ω-dicarboxylic acids having valuable pharmacological activity in the treatment of obesity, hyperlipidemia and maturity-onset diabetes (insulin independent diabetes). The invention also provides pharmaceutical compositions comprising the aforementioed novel derivatives.

Obesity, hyperlipidemia and diabetes have been shown by epidemiological and other studies to play a causal role in atherosclerotic cardiovascular diseases which at present account for more than half of the total deaths in Western society. Thus, these pathological conditions may be regarded as leading factors affecting the mortality and morbidity of our society.

Obesity is still considered to be an "incurable disease", despite the recognized preventive value of weight reduction. Dietary measures were found in most studies to be ineffective for long term weight reduction and the effectiveness of behavior modification in the treatment of obesity is still equivocal. A more drastic solution, a surgical ileojejunal shunt by passing the small intestinal absorptive bed, is considered to be too risky a treatment for obesity. Nor did anorexic drugs prove to be a suitable solution to the problem, because these drugs are known to affect the central nervous system in a non-specific manner and their use has been drastically curbed by Federal Drug authorities of various countries.

The treatment of hypercholesterolemic-hypertriglyceridemic conditions is at present mainly based on low cholesterol dietary intake combined with drug treatment (mostly Clofibrate and its derivatives). However, recent indications of serious and sometimes lethal side effects of Clofibrate have resulted in disapproval of this drug in certain countries, leaving less efficient drugs as therapeutic alternatives.

Insulin-independent diabetes is well correlated with obesity, and overweight is considered to play a critical role in the polygenic etiology of peripheral insulin resistance. The classical pharmacological treatment of this diabetic state consists of increasing the serum insulin content either by insulin delivery or by stimulating insulin secretion. The ensuing hyperinsulinemia results in down-regulation of the insulin-resistant state. Hence, the treatment of insulin-independent diabetes should aim at alleviating insulin resistance with a concomitant normoinsulinemia and up-regulation of peripheral insulin receptors.

α,ω-dialkane dioic acids of chain length of 10 to 14 carbon atoms which are tetra-methyl substituted on the α,α'-carbon atoms, as well as their salts and ester derivatives were disclosed in Creger U.S. Pat. No. 3,773,946 and French No. 2,068,535 as possessing serum triglyceride-lowering activity and serum cholesterol-lowering activity. These known compounds, however, have not proved to be of value in medicine for the treatment of obesity and hypercholesterolemia. The corresponding β,β,β',β'-tetramethylalkanediols, derived from the former diacids by reduction, and their esters were disclosed in the Creger U.S. Pat. No. 3,930,024 and French No. 2,068,534 and alleged to have the same activites.

A novel class of compounds has now been found, in accordance with the present invention, to be surprisingly effective in blocking cholesterol and neutral lipid synthesis in-vivo without adversely affecting energy metabolism. The overall effect of these compounds in-vivo results in significant decrease in blood serum cholesterol and triglyceride levels and significant weight reduction due mainly to reduction of neutral lipid synthesis. The new compounds of the invention were also found to be beneficial for the alleviation of the diabetic trait in insulin-independent diabetes.

The compounds useful in the present invention have the general formula:

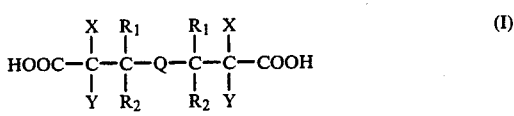

(I)

and in-vivo hydrolyzable functional derivatives of the carboxylic groups thereof, wherein $R_1$ and $R_2$ each independently represents an unsubstituted or substituted hydrocarbyl or heterocyclyl radical; X and Y each independently represents hydrogen, lower alkyl, halogen, carboxy, lower alkoxycarbonyl or carbamoyl, and one of X or Y can also be alkoxy, hydroxy or cyano; and Q represents a diradical consisting of a linear chain of 8 to 14 carbon atoms, one or more of which may be replaced by heteroatoms, said chain being optionally substituted by inert substituents and one or more of said carbon or heteratom chain members optionally forming part of a ring structure.

The term "hydrocarbyl" in the definition of $R_1$ and $R_2$ includes, e.g. lower alkyl optionally substituted by phenyl, hydroxy, lower alkoxy or halogen; alkenyl; alkynyl; cycloalkyl; or phenyl optionally substituted by hydroxy, lower alkoxy, lower alkyl or halogen.

The meaning of Q as a diradical is a linear saturated or unsaturated chain of 8–14 carbon atoms which may be (a) substituted by oxygen, halogen, hydroxy or lower alkoxy,
(b) interrupted by one or more heteroatoms, and/or
(c) of which 1–4 chain members may be part of $C_3$–$C_7$ cycloalkyl or phenyl ring.

Lower alkyl groups suitable as the substituents $R_1$, $R_2$, X and Y are groups with 1–6, especially 1–4 carbon atoms; preferred are methyl and ethyl. Lower alkoxy groups suitable as the substituents $R_1$, $R_2$, X and Y as well as the substituent Q are groups of 1–6, especially 1–4 carbon atoms; again methyl and ethyl are preferred. Lower alkoxy carbonyl groups of substituents X and Y are suitably groups with 1–6 carbon atoms, preferred among which are methoxy-carbonyl and ethoxy carbonyl.

Lower alkenyl groups suitable as the substituents $R_1$ and $R_2$ contain 2–6 carbon atoms; preferred is allyl. Lower alkynyl groups suitable as the substituents $R_1$ and $R_2$ contain 2–6 carbon atoms, and preferred is propynyl. Halogen means in all cases fluorine, chlorine and bromine.

Phenyl can be substituted in all cases by hydroxy, lower alkoxy ($C_1$–$C_6$), lower alkyl ($C_1$–$C_6$) or halogen.

Lower alkyl groups which are substituted by phenyl are preferably benzyl and phenethyl, whereby the phenyl groups can be substituted by the above mentioned substituents. Cycloalkyl groups ($C_3$-$C_7$) of substituents $R_1$ and $R_2$ and as part of Q are preferably cyclopropyl, cyclohexyl and cycloheptyl.

The group Q is usually constructed symmetrically because of the synthesis thereof. Preferred are residues as —(CH$_2$)$_8$—, —(CH$_2$)$_{10}$, —(CH$_2$)$_{12}$— and —(CH$_2$)$_{14}$—. Preferred unsaturated chains are —(CH$_2$)$_4$—CH═CH—(CH$_2$)$_4$— and —(CH$_2$)$_5$—CH═CH—(CH$_2$)$_5$—. A chain Q can be substituted by oxygen, an oxo-oxygen which forms hetero-groups. Preferable is the residue

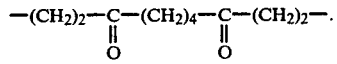

The groups can also be interrupted one or more times by hetroatoms consisting of oxygen, sulphur or nitrogen which may be substituted by lower alkyl ($C_1$-$C_6$) or benzyl. The sulphur atoms can be oxidized to SO or SO$_2$. The following groups are preferred: —(CH$_2$)$_5$—O—(CH$_2$)$_5$—; —(CH$_2$)$_5$—S—(CH$_2$)$_5$—;

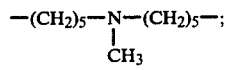

—(CH$_2$)$_2$—S—(CH$_2$)$_4$—S—(CH$_2$)$_2$—. A ring system can be part of a chain Q. This ring system can be saturated (cycloalkylidene) or unsaturated (phenylene). Preferred cycloalkylidene ring systems are cyclopropylidene and cyclohexylidene, which are located at the 1,1-; 1,2-; 1,3- or 1,4-position, e.g. (CH$_2$)$_4$-cyclopropylidene or cyclohexylidene-(CH$_2$)$_4$—. The number of carbon atoms of the total chain is in case of the 1,1 and 1,3-connection uneven. This applies also to chains which are interrupted by one hetro atoms. A phenyl ring may be inserted in 1,2-; 1,3- or 1,4-position in the chain, e.g.:
—(CH$_2$)$_3$—phenyl—(CH$_2$)$_3$—;
—(CH$_2$)$_4$—phenyl—(CH$_2$)$_4$—;
—CH$_2$—CH═CH—phenyl—CH═CH—CH$_2$—; or
—CH$_2$—CH═CH—CH$_2$—Phenyl—CH$_2$—CH═CH—CH$_2$—.

Included within the scope of the invention are those derivatives of the α and/or ω carboxy groups of the compounds of formula I above, which are capable of being hydrolyzed in-vivo to yield the free diacids of formula I. Among such suitable derivatives there should be mentioned, in the first place, salts with pharmaceutically acceptable inorganic or organic cations, in particular alkali metal salts, alkaline earth metal salts, ammonium salts and substituted ammonium salts; esters, particularly lower alkyl esters; amides, mono- and di-substituted amides; and anhydrides, e.g. with lower alkanoic acids; and lactones formed by ring closure of either or both carboxylic groups with a free hydroxy substituent (or substituents) in the molecule of formula (I).

A preferred group of compounds in accordance with the invention are those of formula (I) above in which $R_1$ an $R_2$ are each lower alkyl, Y is hydrogen and Q is a straight polymethylene chain of 8 to 14 carbon atoms; and in-vivo hydrolyzable functional derivatives thereof.

Especially preferred novel compounds of the present invention are those of the general formula:

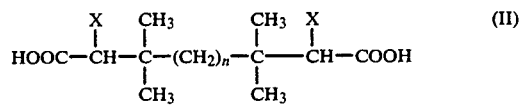

wherein X is hydrogen, lower alkyl, fluoro, chloro, bromo or cyano and n is an integer from 8 to 14 with the proviso that when X is H, cyano or ethoxycarbonyl, n is not 8; and their in-vivo hydrolyzable functional derivatives.

The novel compounds of formula (I) according to the invention, can be prepared by methods known per se, some of which are illustrated in the examples herein. Compounds of formula I can be prepared in known manner by (a) transferring a dihalogen compound of formula VIII

in which Hal means chlorine or bromine and Q has the same meaning as above, in a bis-Grignard compound and reacting, the obtained compound with two mols of a compound of formula III

in which $R_1$ and $R_2$ have the same meaning as above, $R_3$ represents a lower alkyl group and U is a COOR$_3$-group or a —CONH$_2$ or CN-group, or (b) by reacting a bis-triphenylphosphonium compound of formula IV

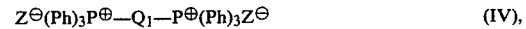

in which Z is chloride or bromide, and Q is a linear, saturated or unsaturated alkylene chain with 2-12 carbon atoms, which may be (aa) substituted by oxygen, halogen, hydroxy or lower alkoxy,
(bb) interrupted by one or more heteroatoms and/or
(cc) of which up to 4 members of the linear chain can be part of a $C_3$-$C_7$ cycloalkyl or a phenyl ring,
with 2 mols of carboxylic acid ester of formula V

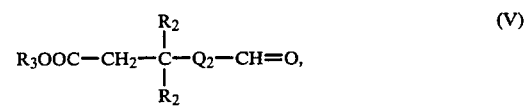

in which $R_1$ and $R_2$ have the same meaning as above, $R_3$ represents a lower alkyl group and $Q_2$ is a valency bond or an alkylene chain with up to 5 carbon atoms, with the proviso that in the reaction product $Q_1$ and two $Q_2$ together do not form a chain consisting of less than 8 carbon atoms or more than 14 carbon atoms, whereupon the obtained compounds of formula I may be converted to other compounds of formula I, and obtained esters, amides or salts may be converted into their free acids, or free acids may be converted into salts, esters or amides.

Process (a) usually leads to tetraesters. These compounds may be hydrolized by alkali and subsequently decarboxylated by heating. The resulting compounds with X, Y=hydrogen may be halogenated in the α,α'-position. This can be done by direct fluorination, bromination or chlornation or by the appropriate halogen N-succinamide. Alkyl groups are normally introduced by appropriate alkyl halides after reaction, e.g. with n-butyl-lithium.

According to process (b) the bis-phosphonium salt of formula IV reacts with 2 mols of carboyxlic acid ester of formula V in the presence of strong bases, e.g. NOH or sodium methylate, whereby there results a diester of an at least doubled unsaturated Q chain. The residue $Q_1$ may substituted, interrupted or part of a ring system analogous to Q. Instead of the bis-phosphonium salt of formula IV appropriate phosphine oxides or phosphonic acid esters may be used.

Process (b) can be used preferably to obtain compounds with a residue Q which contains a phenylene or cycloalkylidene part or is interrupted by hetero atoms. The resulting unsaturated compounds may be hydrogenated subsequently to the corresponding saturated compounds. Analogously, phenylene compounds may be hydrogenated to cyclohexylidene compounds.

The phenylene or cycloalkylidene compounds may also be pepared by reacting a compound of formula VI

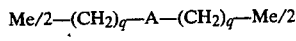

$$Me/2-(CH_2)_q-A-(CH_2)_q-Me/2 \quad (VI),$$

in which
Me is a metal consisting of cadmium or zinc
A is phenylene or $C_3$-$C_7$ cycloalkylidene and
q is 1 or 2,
with a compound of formula VII

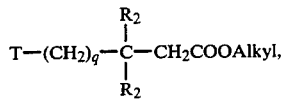

$$T-(CH_2)_q-\underset{\underset{R_2}{|}}{\overset{\overset{R_2}{|}}{C}}-CH_2COOAlkyl, \quad (VII)$$

in which T is an active carboxyclic acid residue, e.g. acid halide or acid anhydride, and $R_1R_2$ and q have the same meaning a above, and subsequently if desired hydrolyzing the resulting diketo-esters and reducing the kito groups.

The olefines may be obtained by using as strong bases alkali-metal alcoholates, e.g. lithium or sodium methylate; alkali amides, e.g. sodium amide; or organo-metallic (e.g. lithium) compounds, e.g. n-butyl lithium or sodium hydride. The reaction medium is preferably alcohol, ether e.g. diethylether or tetrahydrofuran.

The hydrogenation of the bis-alkene resulting from process (b) occurs under usual conditions in the presence of metal catalysts, e.g. palladium/charcoal at normal pressure; preferred are use of pressure greater than atmospheric and temperature above ambient.

Useful catalysts for the hydrogenation of the phenyl ring are platinum, rhodium or ruthenium. Keto groups of diketo acids or esters resulting in process (a) are reduced preferably analogously to the Huang-Minlon-process (heating a mixture consisting of a ketone, diluted alkali, glycol and hydrazine) or by the Clemmensen reduction (in the presence of zinc or copper containing zinc and hydrochloric acid). It is also possible to transfer the keto compounds to tosyl hydroasones which are subsequently reduced by complex alkali metal boron hydrides.

A known compound useful in the present invention is 1,4-phenylene-bis-(3,3-dimethyl-5-yl-pentanoic acid), described by A. T. Blomquist et al [Am. Soc. 80 (1958) 3405], no pharmaceutical utility disclosed.

Novel compounds useful in the invention, besides those set forth in the working examples below, are:
(1) 2,3,3,14,14,15-hexamethyl-hexadecane-1,16-dioic acid
(2) 2,15-di-carbamoyl-3,3,14,14,-tetramethyl-hexadecane-1,16-dioic acid
(3) 3,14-diethyl-3,14-dimethyl-hexadecane-1,16-dioic acid
(4) 3,3,14,14-tetra-(2-propenyl)-hexadecane-1,16-dioic acid
(5) 3,3,14,14-tetra-cyclohexyl-hexadecane-1,16-dioic acid
(6) 2,15-dibromo-3,3,14,14-tetraphenyl-hexadecane-1,16 dioic acid
(7) 1,2-cyclopropylidene-bis-(3,3-dimethyl-7-yl-heptanoic acid)
(8) 9,9-pentamethylene-3,3,15,15-tetramethyl-heptadecane-1,17-dioic acid
(9) 1,2-cyclohexylidene-bis-(3,3-dimethyl-7-yl-heptanoic acid)
(10) 1,2-phenylene-bis-(3,3-dimethyl-7-yl-heptanoic acid)
(11) 3,3,15,15-tetramethyl-9-thia-heptadecane-1,17-dioic acid
(12) 9-oxa-3,3,15,15-tetramethyl-heptadecane-1,17-dioic acid
(13) 9-aza-3,3.9,15,15-pentamethyl-heptadecane-1,17 dioic acid
(14) 3,3,14,14-tetramethyl-6,11-dithiahexadecane-1,16 dioic acid
(15) 2,15-difluoro-3,3,14,14-tetramethyl-hexadecane-1,16-dioic acid
(16) 2,2,15,15-tetrafluoro-3,3,14,14-tetramethyl-hexadecane-1,16-dioic acid
(17) 2,2,15,15-tetrachloro-3,3,14,14-tetramethyl-hexadecane-1,16-dioic acid
(18) 2,2,15,15-tetrafluoro-3,3,14,14-tetramethyl-hexadecane-1,16-dioic acid
(19) 3,3,14,14-tetrahydroxymethyl-11,16-dioic acid
(20) 2,15-dichloro-3,14-di(chloromethyl)-3,14-dimethyl-hexadecane-1,16-dioic acid
(21) 2,15-dichloro-3,3,14,14-tetra(chloromethyl)-hexadecane-1,16-dioic acid
(22) 3,3,14,14-tetra-(4-hydroxyphenyl)-hexadecane-1,16-dioic acid
(23) 3,3,14,14-tetra-(4-chlorophenyl)-hexadecane-1,16-dioic acid
(24) 3,3,14,14-Tetra-(4-methyl-phenyl)-hexadecane-1,16-dioic acid
(25) 3,3,14,14-tetra-(4-methoxy-phenyl)-hexadecane-1,16-dioic acid In another aspect, the present invention provides pharmaceutical compositions for the treatment of obesity, hyperlipidemia and diabetes, comprising as active ingredients the compounds of formula (I) above together with pharmaceutical carriers or diluents. The pharmaceutical compositions are primarily for oral administration, but may also be for parenteral administration. These pharmaceutical compositions, which are preferably in dosage unit form, may be in the form of, e.g. tablets, capsules, lozenges, pills, powders and aqueous and non-aqueous solutions or suspensions. The pharmaceutical compositions of this invention preferably comprise also conventional pharmaceutical solid or liquid carriers or diluents, e.g. gelatin, sugars, starches, cellulose derivatives, fatty acids and their salts, vegetable oils, glycerine, glycols, water, aqueous saline or phosphate buffer solutions and the like. The compositions may also comprise other compatible substances normally used in pharmaceutical formulations and also other additives, such as coloring agents, flavoring agents and preservatives.

The pharmaceutical compositions according to the invention are preferably in dosage unit form, each unit containing from 50 to 500 mg of the active ingredient of the formula (I) above. The daily dosage of the compounds of formula (I) above according to the invention will depend on the age, needs and tolerance of the individual patient, but will usually range from 50 mg to from 5000 mg per day.

The preparation of some of the novel compounds of formula (I) according to the invention is illustrated in the following non-limiting Examples.

EXAMPLE 1

1,1,14,14-Tetra(ethoxycarbonyl)-2,2,13,13-tetramethyl-tetradecane

The bis-Grignard reagent prepared from 3.5 g of Mg turnings and 21.0 g of 1,10 -dibromodecane in 90 ml of tetrahydrofuran (THF), was added dropwise by means of a syringe to a stirred suspension of 0.25 g of $Cu_2Cl_2$ and 25.0 g of diethyl isopropylidenemalonate in 50 ml of dry THF cooled to $-70°$ C. The reaction mixture was allowed to gradually reach room temperature under stirring and the stirring was continued at that temperature for 16 hours. The reaction mixture was then poured into a mixture of 100 ml of concentrated hydrochloric acid and 150 g of ice, under vigorous stirring, then diluted with water and extracted thrice with diethyl ether. The ether extracts were combined, washed with water and with a 10% solution of sodium carbonate and dried over anhydrous magnesium sulfate. The ether solution was filtered and evaporated to dryness. 34.0 g of the title compound were obtained and proved to be pure on this layer chromatography.

NMR ($CDCl_3$): 4.17 (q, J=7 $H_z$, 8H); 3.30 (s, 2H); 1.27 (br.s, 32H); 1.10 (br.s, 12H).

EXAMPLE 2

1,1,16,16-Tetra(ethoxycarbonyl)-2,2,15,15-tetramethyl-hexadecane

The procedure of Example 1 was followed except that for the preparation of the bis-Grignard reagent 23.0 g of 1,12-dibromododecane were used instead of the dibromodecane.

The title compound was obtained in a yield of 25.0 g and gave a single spot on thin layer chromatography.

NMR ($CDCl_3$): 4.12 (q, J=8 $H_z$, 8H); 3.30 (s. 2H); 1.23 (br.s, 36H); 1.06 (br.s, 12H).

EXAMPLE 3

1,1,12,12-Tetra(ethoxycarbonyl)-2,2,11,11-tetramethyl-dodecane

The procedure of Example 1 was followed except that the bis-Grignard reagent was prepared from 17.0 g of 1,8-dibromooctane instead of the dibromodecane used in Example 1. 30.2 g of the title compound were obtained. On thin layer chromatography the product gave a single spot.

NMR ($CDCl_3$): 4.20 (q, J=8 $H_z$, 8H); 3.30 (s, 2H). 1.20 (br.s, 28H); 1.10 (br.s, 12H).

Schisla et al [J. Org. Chem. 35 (1970) 3324–3230], no pharmaceutical utility disclosed.

EXAMPLE 4

3,3,14,14-Tetramethyl-hexadecane-1,16-dioic acid

A mixture of 17.0 g of the tetra-ester of Example 1 and 300 ml of a 25% aqueous KOH solution was heated in an oil bath to reflux temperature and the mixture was refluxed until the organic phase has completely disappeared (about 48 hours). The aqueous solution was then cooled to room temperature, extracted with ether, further cooled by the addition of ice and acidified with concentrated aqueous hydrochloric acid, whereupon a solid precipitate was formed consisting of the corresponding tetracarboxylic acid. This solid precipitate was dissolved in diethyl ether and the solution dried over anhydrous magnesium sulfate, filtered and evaporated to dryness. The tetracarboxylic acid residue was decarboxylated by heating to 150°–160° C. on an oil bath until evolution of carbon dioxide was no longer observed. The crude product was cooled and recrystallized from a mixture of chloroform and petroleum ether (40°–60° C.). The pure product was obtained at a yield of 5.5 g.

NMR ($CDCl_3$): 11.06 (br.s, 2H); 2.23 (s, 4H); 1.28 (s, 20H); 1.03 (s, 12H).

EXAMPLE 5

3,3,16,16-Tetramethyl-octadecane-1,18-dioic acid

When the tetra-ester product of Example 2 is submitted to hydrolysis and decarboxylation by the procedure of Example 4, the title compound is obtained.

NMR ($CDCl_3$): 2.28 (s, 4H); 1.33 (s, 24H); 1.03 (s, 12H).

EXAMPLE 6

3,3,12,12-Tetramethyl-tetradeca-1,14-dioic acid

By the procedure of Example 4, the title compound is obtained from the tetra-ester prepared in accordance with Example 3.

NMR ($CDCl_3$): 2.28 (s, 4H); 1.33 (s, 16H); 1.07 (s, 12H).

Schisla et al [J. Org. Chem. 35 (1970) 3324–3230], no pharmaceutical utility disclosed.

EXAMPLE 7

1,14-Di-(ethoxycarbonyl)-1,14-dicyano-2,2,13,13-tetramethyl-tetradecane

The procedure of Example 1 was followed except that instead of diethyl isopropylidenemalonate, there were used 19.1 g of ethyl isopropylidenecyanoacetate. The crude product was applied to the top of a dry column containing 1 kg of silica and eluted with 10% diethyl ether in petroleum ether (60°–80° C.). 30.1 g of the title compound were obtained.

NMR ($CDCl_3$): 4.252 (q, J=8 $H_z$, 4H); 3.370 (s, 2H); 1.297 (t, J=8 $H_z$, 6H); 1.275 (br.s, 20H) 1.143 (s, 6H); 1.107 (s, 6H).

I.R.: 2250, 1750 $cm^{-1}$.

EXAMPLE 8

2,15-Dicyano-3,3,14,14-tetramethyl-hexadecane-1,16-dioic acid

The bis-cyano ester prepared in accordance with Example 7 was gently refluxed in a 10% aqueous KOH solution until the oil layer disappeared. The title compound was obtained in TLC purity.

NMR (CDCl$_3$): 7.88 (br.s, 2H); 3.46 (s, 2H); 1.25 (s, 20H); 1.11 (br.s, 12H).

IR: 2260, 1730 cm$^{-1}$.

EXAMPLE 9

2,15-Dibromo-3,3,14,14-tetramethyl-hexadecane-1,16-dioic acid 3,3,14,14-Tetramethyl-hexadecane-1,16-dioic acid prepared as described in Example 4 was dissolved in 2 ml of dry CCL, and 5.8 ml of SOCl$_2$ were added. The mixture was heated to 65° C. for 30 minutes, cooled to room temperature and 10 ml of additional dry CCl$_4$ were added, followed by 2 drops of 48% hydrobromic acid and, slowly, 4.3 g of N-bromo-succinimide (NBS). The mixture was heated for 10 minutes at 70° C. and thereafter for one more hour at 85° C. The reaction mixture was cooled, filtered and evaporated to dryness. The crude bis-(alpha-bromoacid chloride) product was added dropwise to a 10% aqueous solution of KOH, the solution was stirred for 1 hour and then acidified and extracted thrice with diethyl ether. The ether extracts were combined, dried over anhydrous magnesium sulfate and filtered. Evaporation to dryness yielded the crude title compound which was purified on preparative thin layer chromatography plates (silica), developed with 3% methanol in methylene dichloride. 1.5 g of the pure title compound were obtained.

NMR (CDCl$_3$): 8.65 (br.s, 2H); 4.21 (s, 2H); 1.33 (br.s, 20H); 1.15 (s, 12H).

IR: 1750, 1140, 1010, 725, 660 cm$^{-1}$.

EXAMPLE 10

2,3,3,14,14,15-Hexamethyl-hexadecane-1,16-dioic acid 70 ml of a 15% solution of n-butyllithium in hexane was added dropwise by a syringe to a stirred mixture of 70 ml of THF and 14 ml of redistilled diisopropylamine, at −20° C. under a nitrogen atmosphere. After stirring for 30 minutes, 7.5 g of 3,3,14,14-tetramethyl-hexadecane-1,16-dioic acid (prepared in Example 4) in 10 ml of dry THF were added to the reaction mixture, the temperature being maintained below −10° C. The reaction mixture was allowed to warm slowly to 50° C. and maintained at that temperature for 2 hours, thereafter cooled to −20° C. and 5.4 g of methyl iodide were added at such a rate as to keep the temperature below 0° C. The reaction mixture was then heated to 40° C. for one hour and then poured into an ice cold 10% solution of hydrochloric acid. The mixture was extracted twice with methylene chloride, washed with 10% aqueous hydrochloric acid and with water and dried over anhydrous magnesium sulfate. The crude product was purified by chromatography on a silica column the eluent being a 3% solutuon of methanol in methylene chloride.

NMR (CDCl$_3$): 11.33 (br.s, 2H); 2.43 (q, J=8 H$_z$, 2H); 1.25 (br.s, 20H); 1.13 (d, J=8 H$_z$, 6H); 0.91 (s, 12H).

EXAMPLE 11

1,14-Diethoxycarbonyl-2,2,13,13-tetramethyl-tetradecane 3.42 g of 3,3,14,14-tetramethylhexadecane-1,16-dioic acid were converted to the corresponding diacid chloride by reaction with 5.8 ml of SOCl$_2$ and the crude diacid chloride was added under stirring to 30 ml of absolute ethanol. The solution was evaporated to dryness whereupon 3.4 g of the title compound were obtained.

NMR (CDCl$_3$): 4.13 (q, J=7 H$_z$, 4H); 2.23 (s, 4H); 1.30 (s, 26H); 1.00 (s, 12H).

IR: 1735, 760 cm$^{-1}$.

EXAMPLE 12

1,14-Di-(ethoxycarbonyl)-1,14-dibromo-2,2,13,13-tetramethyl-tetradecane

The title compound was prepared by the procedure of Example 11 from the bis-acid chloride of the α,α'-dibromodiacid of Example 9.

NMR (CDCl$_3$): 4.20 (s, 2H); 3.73 (s, 6H); 1.27 (s, 20H); 1.07 (s, 12H).

EXAMPLE 13

1,14-Bis-carbamoyl-2,2,13,13-tetramethyl-tetradecane

The bis-acid chloride of 3,3,14,14-hexadecane-1,16-dioic acid, prepared as described in Example 11 was added under stirring to an ice-cold saturated solution of ammonia in dry methanol. 3.3 g of the bis-amide title compound were obtained.

NMR (CDCl$_3$): 5.43 (br.s, 4H); 2.10 (s, 4H); 1.30 (s, 20H); 1.00 (s, 12H).

IR: 3440, 3190, 1660, 1625 cm$^{-1}$.

EXAMPLE 14

2,15-dichloro-3,3,14,14-tetramethylhexadecane-1,16-dioic acid 0.128 g of 3,3,14,14-tetramethylhexadecane-1,16-dioic acid prepared as described in Example 4 was dissolved in 2 ml of SOCl$_2$. The mixture was refluxed for 2 h followed by the addition of 2 ml of SOCl$_2$ and 0.162 g of N-chlorosuccinimide (NCS). The mixture was further refluxed for 4½ more hours, evaporated to dryness and the crude product was dissolved in CCl$_4$ and filtered. The filtrate was evaporated to dryness and the crude bis-(alpha chloroacid-chloride) was subjected to silicic acid chromatography with petrol ether as eluent. 87% yield.

NMR (CDCl$_3$): 4.46 (s, 2H); 1.34 (m, 20H); 1.00 (s, 6H); 0.97 (s, 6H).

The bis-(alpha-chloroacid chloride) was hydrolyzed quantitatively by boiling with water for 16 h. The reaction mixture was then extracted with chloroform and the chloroform extract was dried over anhydrous magnesium sulfate, filtered and evaporated to dryness to yield the crude title compound. The crude product was dissolved in bicarbonate solution, acidified to pH 2.0, and extracted with chloroform. The chloroform extract was dried over anhydrous magnesium sulfate, evaporated to dryness and was further dried in high vacuum for 24 h. The solidified product was crystalized from petrol ether. m.p. 103°–112° C.

NMR (CDCl$_3$): 4.17 (s, 2H); 1.26 (m, 20H); 1.00 (s, 12H).

Analysis: %C 58.12 (Calc. 58.38); %H 8.70 (Calc. 8.82).

EXAMPLE 15

2,15-dibromo-3,3,14,14-tetramethylhexadecane-1,16-dioic acid

An alternative procedure to Example 9.

5.0 g of 3,3,14,14-tetramethylhexadecane-1,16-dioic acid prepared as described in Example 4 were dissolved in 10 ml of SOCl$_2$. The mixture was heated to 75° C. for 60 min., cooled and 45 ml of $CCl_4$ were then added followed by 8 ml of bromine. The mixture was further refluxed for 16 h while being illuminated by a tungsten lamp of 150 W. The reaction mixture was cooled to room temperature, excess bromine was evaporated and the crude product was flash chromatographed on 400 mesh silicic acid to yield the bis-(alpha-bromoacid chloride). 89% yield.

NMR ($CDCl_3$): 4.47 (s, 2H); 1.26 (m, 20H); 1.11 (s, 6H).

The bis-(alpha-bromoacid chloride) was hydrolyzed quantitatively by refluxing in water for 16 h. The hydrolysis mixture was extracted with ether. The ether extract was washed extensively by water, dried over anhydrous magnesium sulfate and was evaporated to dryness. Further purification of the acid was accomplished by conversion into the disodium salt followed by acidification with dilute hydrochloric acid.

NMR ($CDCl_3$): 4.18 (d, 2H); 1.405 (m, 4H); 1.25 (m, 16H); 1.13 (s, 6H); 1.09 (s, 6H).

Analysis: %C, 48.16 (Calc. 48.00); %H, 6.96 (Calc. 7.20).

EXAMPLE 16

2,15-dihydroxy-3,3,14,14-tetramethylhexadecane-1,16-dioic acid 0.2 g of 2,15-dichloro-3,3,14,14-tetramethylhexadecane-1,16-dioyl chloride prepared as described in Example 14 was dissolved in 10 ml of 30% KOH solution. The mixture was boiled for 3 h, cooled and acidified to pH 2.0. The precipitate was collected by filtration and dissolved in ethyl acetate. It crystalized upon adding petrol ether. m.p. 87°–100° C. 61% yield.

NMR ($CDCl_3$): 3.90 (s, 2H); 1.18 (m, 20H); 0.90 (s, 12H).

Analysis: %C 64.24 (Calc. 64.17); %H 10.15 (Calc. 10.16).

EXAMPLE 17

1,14-di-(carbomethoxy)-1,14-dibromo-2,2,13,13-tetramethyltetradecane 1.28 g of 2,15-dibromo-3,3,14,14-tetramethyl hexadecane-1,16-dioyl chloride prepared as described in Example 15 was dissolved in 50 ml of absolute methanol. The mixture was refluxed for 16 h, then evaporated to dryness and the crude product was dissolved in chloroform. The chloroform phase was washed with bicarbonate solution, water, dried over anhydrous sulfate and was evaporated to dryness. 40% yield.

NMR ($CDCl_3$): 4.16 (s, 2H); 3.72 (s, 6H); 1.24 (m, 20H); 1.07 (s, 6H); 1.05 (s, 6H).

EXAMPLE 18

1,14-di-(carbomethoxy)-1,14-dichloro-2,2,13,13-tetramethyltetradecane 1.28 g of 1,15-dichloro-3,3,14,14-tetramethylhexadecane-1,16-dioylchloride prepared as described in Example 14 was dissolved in 50 ml of absolute methanol. The mixture was refluxed for 16 h, then evaporated to dryness and the crude product was dissolved in chloroform. The chloroform phase was washed with bicarbonate solution, water, dried over anhydrous magnesium sulfate and was evaporated to dryness. 40% yield.

NMR ($CDCl_3$): 4.15 (s, 2H); 3.70 (s, 6H); 1.20H); 1.05 (s, 12H).

EXAMPLE 19

2,15-dimethoxy-3,3,14,14-tetramethylhexadecane-1,16-dioic acid 1.21 g of 2,15-dibromo-3,3,14,14-tetramethylhexadecane-1,16-dioic acid prepared as described in Example 15 was dissolved in 50 ml of methanol containing 0.58 g of sodium methoxide. Containing the addition of 64 ml of $H_2O$ mixture was heated at 60° C. for 4 days. The solvent was then evaporated to dryness and the crude product was dissolved in water, washed with ether, acidified by HCl and extracted into ether. The ether extract was dried over anhydrous magnesium sulfate and was evaporated to dryness to yield the title compound. 61% yield.

NMR ($CDCl_3$): 3.47 (s, 2H); 3.39 (s, 6H); 1.24 (m, 20H); 0.95 (d, 12H).

IR: 3000, 1712, 1120 $cm^{-2}$.

Analysis: %C 65.51 (Calc. 65.67); %H 10.60 (Calc. 10.45).

EXAMPLE 20

1,1,18,18-tetra(carboethoxy)-2,2,17,17-tetramethyloctadecane

The procedure of Example 1 was followed except that the bis-Grignard reagent was prepared from 3.0 g of 1,14-dibromotetradecane and 0.75 g of Mg turnings in 40 ml of dry THF. The bis-Grignard reagent was then added dropwise to a stirred suspension of 0.031 g CuCl and 3.72 g of diethyl isopropylidenemalonate in 15 ml of dry THF. The addition product was protonated and extracted into ether as in Example 1 followed by silicic acid (400 mesh) chromatography in benzene:-petrol ether 1:2.5 to yield the title compound. 86% yield.

NMR ($CDCl_3$): 4.3 (q, 8H); 3.5 (s, 2H); 1.5 (m, 40H); 1.1 (m, 12H).

EXAMPLE 21

3,3,18,18-tetramethyleicosane-1,20-dioic acid

The tetraester of Example 20 was hydrolyzed and decarboxylated quantitatively as described in Example 4.

NMR ($CDCl_3$): 2.22 (s, 4H); 1.25 (m, 28H); 0.995 (s, 12H).

EXAMPLE 22

3,3,14,14-tetramethyl-8-hexadecane-1,16-dioic acid 40 g of dimedone was dissolved in 60 ml of 20% KOH solution followed by the addition of 33 g of 1,4-dibromobutene, 1.4 of copper powder prepared by the reduction of CuO and 14 ml of 20% KOH solution. The mixture was stirred for 4 d followed by dissolving the solidified product in 10% NaOH. The basic solution was filtered, the filtrate was extracted with ether and acidified to precipitate the 1,4-bis-dimedone-2-butene condensation product. 1,4-bis-dimedone-2-butene was crystallized from acetone. m.p. 205°–206° C.

NMR (DMSO): 5.20 (m, 2H); 2.72 (m, 4H); 2.20 (s, 8H); 1.025 (s, 6H).

Analysis: %C 72.29 (calc. 72.12): %H 8.43 (calc. 8.69).

Mass spectroscopy: molecular ion—332.

8.0 g of 1,4-bis-dimedone-2-butene, 6 ml of 85% hydrazine hydrate and 5 ml of methanol were added to a solution of 5 g NaOH in 50 ml of triethyleneglycol. The mixture was heated at 120° C. for 36 h, then heated to 195° C. with the evaporation of water followed by reflux for 20 h. The mixture was cooled, diluted with water, extracted with ether, acidified and extracted into $CH_2Cl_2$. The dichloromethane extract was washed with water, dried over anhydrous magnesium sulfate, evaporated to dryness and further purified by silicic acid chromatography in 20:1 dichloroethane:methanol to yield the title compound. The title compound was crystalized from petrol ether. m.p. 100°–101° C.

NMR ($CDCl_3$): 5.38 (quint, 2H); 1.99 (q, 4H); 1.31 (m, 12H); 1.01 (s, 12H).

Analysis: %C 70.54 (Calc. 70.59); %H 10.78 (Calc. 10.59).

EXAMPLE 23

3,3,14,14-tetraphenyl-6,11-diketohexadecane-1,16-dioic acid

The bis-Grignard reagent prepared from 0.49 g of 1,4-dibromobutane and 0.7 g of Mg turnings in 15 ml of dry THF was added dropwise to a stirred suspension of 2.0 g of 4,4-diphenylcyclohexanone [J. Org. Chem., 28, 2544, (1968)] in 20 ml of dry THF. The reaction mixture was refluxed for 16 h, cooled, poured into a mixture of hydrochloric acid and ice, then diluted with water and extracted with diethylether. The ether extract was washed with water, dried over anhydrous magnesium sulfate and evaporated to dryness to yield 1,4-bis(4,4-diphenyl-1-cyclohexanol)-butane.

NMR ($CDCl_3$): 7.08–7.36 (m, 20H); 2.38 (m, 8H); 1.55 (m, 8H); 1.23 (m, 8H).

0.5 g of 1,4-bis(4,4-diphenyl-1-cyclohexanol)butane was dissolved in 40 ml of acetic acid followed by the addition of 3.0 g of $CrO_3$ in small portions. The mixture was kept at room temperature for 16 h, was then poured on ice, and this was followed by extraction with ether. The ether extract was extracted with sodium bicarbonate solution, and the latter acidified and extracted with ether. The extract was dried over anhydrous magnesium sulfate and evaporated to dryness to yield the title compound. 50% yield.

NMR ($CDCl_3$): 9.90 (br.s, 2H); 7.13 (m, 20H); 1.9–3.0 (m, 20H).

EXAMPLE 24

3,3,14,14-tetraphenylhexadecane-1,16-dioic acid 0.27 g of 3,3,14,14-tetraphenyl-6,11-diketohexadecane-1,16-dioic acid prepared as described in Example 23 and 0.23 ml of 85% hydrazine hydrate were added to a solution of 0.4 g KOH in 10 ml of triethyleneglycol. The mixture was heated at 120° C. for 24 h, then heated to 195° C. with the evaporation of water followed by reflux for 7 h. The mixture was cooled, diluted with water, extracted with ether, acidified and extracted into ether. The ether extract was washed with water, dried over anhydrous magnesium sulfate and evaporated to dryness to yield the title compound. 58% yield.

NMR ($CDCl_3$): 9.7 (s, 2H); 7.16 (m, 20H); 3.05 (s, 4H); 1.2–2.6 (m, 20H).

IR: 3050; 1700 cm$^{-1}$.

EXAMPLE 25

1,4-phenylene-bis-[(1,1-dimethyl-but-4-yl)-dipropionic acid dimethyl ester]

A Grignard solution produced from 3.3 g magnesium turnings, 20.0 g (62.5 mmol) 1,4-bis-(3-bromopropyl)-benzene and 150 ml absolute tetrahydrofuran is added dropwise to a solution consisting of 25.6 g (124 mmol) isopropylidene malonic acid diethylester at −20° C. and is subsequently kept for 2–3 hours at reflux temperature. The cooled mixture is poured into acidified ice water. The aqueous phase is separated off, extracted twice with ether and the combined organic phase is washed with sodium carbonate solution, dried with $Na_2SO_4$ and evaporated. The residue left after evaporation is heated at 0.01 bar to about 150° C. to remove volatile secondary products and there remains 23.6 g (67% theoretical yield) of a viscous oil. Purification of a small amount of a small amount by means of HPLC gave a viscous oil that had an TLC-precoated Merck silica gel 60/F 254 plates of 0.8 in n-heptane-ethyl acetate 1:1 and of 0.5 in n-heptane-ethyl acetate 2:1.

EXAMPLE 26

1,4-phenylene-bis-[(1,1-dimethyl-but-4-yl)-dipropionic acid)]

A mixture consisting of 2.5 g (4.4 mmol) of the tetraethyl ester from example 25, 25 ml methanol and 1.0 g (25 mmol) sodium hydroxide are heated under reflux for 60 hours, then cooled, water is added and extraction with ether carried out. The mixture is then acidified and the acid initially separtes as an oil.

After crystallization, the material is filtered off, washed with water and dried. Yield 1.8 g (90% of the theoretical); melting point 181°–183° C. (with decomposition).

NMR (DDMSO): δ=1.03 (s, 12H); 1.40–1.60 (m, 8H); 2.48 (m, 4H); 3.12 (s, 2H); 7.07 (s, 4H).

EXAMPLE 27

1,4-phenylene-bis-(3,3-dimethyl-6-yl-hexanoic acid)

The named product is obtained by heating 1.4-phenylene-bis-[(1,1-dimethyl-but-4-yl)-dipropionic] (example 26) for 2 hours under nitrogen at 160° C.

Yield 31% of the theoretical; melting point 119°–121° C. (cyclohexane).

NMR (DDMSO): δ=0.93 (s, 12H): 1.30 (m, 4H); 1.53 (m, 4H); 2.08 (s, 4H); 2.49 (t, 4H); 7.067 (4H).

EXAMPLE 28

(a) 1,4-phenylene-bis-(3,3-dimethyl-6-yl-5-hexenoic acid methyl ester)

A sodium methylate solution prepared from 0.92 g (40 mg atom) sodium and 50 ml absolute methanol is added dropwise to a mixture consisting of 6.3 g (40 mmol) 3,3-dimethyl-5-oxopentanoic acid methyl ester, 60 ml absolute methanol and 14.0 g (20 mmol) 1-,4-phenylene-bis-(methyltriphenyl-phosphonium chloride) at room temperature, and the mixture is stirred for 3 hours at room temperature and then evaporated. The residue is dissolved in methylene chloride, filtered and again evaporated. After column chromatography (to remove a small quantity of fluorescent material) using $CH_2Cl_2$/silica gel, 3.8 g (49% of the theoretical yield) of a colorless oil is obtained.

Isomeric mixture

NMR ($CDCl_2$): 1.02 (12H); 2.00–2.55 (8H); 3.58 and 3.63 (6H); 5.23–6.83 (4H); 7.27 (4H).

(b) 1,3-phenylene-bis-(3,3-dimethyl-6-yl-5-hexenoic acid methyl ester)

This compound is obtained in a manner analogous to Example 28a) from 3,3-dimethyl-5-oxo-pentanoic acid methyl ester and 1,3-phenylene-bis-(methyltriphenyl-phosphonium chloride).

Yield 60% of the theoretical; oily product
Isomeric mixture
NMR (CDCl₃): δ=1.05 (12H); 2.15-2.50 (8H); 3.58 and 3.67 (6H); 5.25-6.73 (4H); 7.23 (4H).

EXAMPLE 29

(a) 1,4-phenylene-bis-(3,3-dimethyl-6-yl-hexanoic acid methyl ester)

A mixture consisting of 2.0 g 1,4-pehnylene-bis-(3,3-dimethyl-6-yl-5-hexenoic acid methyl ester) from Example 28a, 50 ml ethanol and a spatula tip of 10% Pd on charcoal catalyser is hydrated in a shaking apparatus at normal pressure until completion of the hydrogen uptake. After filtering off the catalyst, the solution is evaporated and 1.5 g (74% of the thoretical yield) of a colorless oil is obtained.

NMR (CDCl₃): δ=0.97 (s, 12H); 1.17-1.78 (m, 8H); 2.17 (s, 4H); 2.37-2.70 (m, 4H); 3.60 (s, 4H); 7.07 (s, 4H).

(b) 1,3-phenylene-bis-(3,3-dimethyl-6-yl-hexanoic acid methyl ester)

This compound is obtained in a manner analogous to Example 29(a) by hydration of 1,3-phenylene-bis-(3,3-dimethyl-6-yl-hexenoic acid methyl ester), example 28(b).

Yield 94% of the theoretical; colorless oil.
NMR (CDCl₃): δ=0.98 (s, 12H); 1.10-1.93 (m, 8H); 2.20 (s, 4H); 2.38-2.73 (m, 4H); 3.63 (6H); 6.83-7.23 (m, 4H).

EXAMPLE 30

(a) 1,4-phenylene-bis-(3,3-dimethyl-6-yl-hexanoic acid)

A mixture consisting of 0.5 g of the methyl ester (example 29(a)), 5 ml methanol and 5 ml 2N—NaOH is heated for 3 hours at 90° C., then the methanol is distilled off, water is added and the mixture is extracted with ether. The aqueous phase is then acidified and extracted with ether, and the ether extract dried with Na₂SO₄. After evaporation 0.4 g (86% of the theoretical yield) of a product with a melting point 120°-121° C. (cyclohexane) is obtained. The product is identical to that obtained according to example 27.

(b) 1,3-phenylene-bis-(3,3-dimethyl-6-yl-hexanoic acid)

This compound is obtained in a manner analogous to Example 30(a) by hydrolysis of its methyl ester (example 29(b)).

Yield 91% of the theoretical; colorless oil.
NMR (DDMSO): δ=0.93 (s, 12H); 1.30 (m, 4H); 1.53 (m, 4H); 2.07 (s, 4H); 2.49 (t, 4H); 6.92-7.00 (m, 3H); 7.15 (t, 1H).

EXAMPLE 31

(a) 1,4-(cyclohexylidene-bis-(3,3-dimethyl-6-yl-hexanoic acid methyl ester)

A mixture consisting of 0.7 g 1,4-phenylene-bis-(3,3-dimethyl-6-yl-hexanoic acid-methyl ester), example 29(a) and a 50 ml methanol are hydrated in the presence of ruthenium (IV) oxide at 90° C. and 80 bar. The solution is then filtered and evaporated.

Yield 0.7 g (98% of the theoretical); colorless oil.
NMR (CDCl₃): δ=0.97 (s, 12H); 1.10-150 (m, 22H); 2.18 (s, 4H); 3.65 (6H).

(b) 1,3-cyclohexylidene-bis-(3,3-dimethyl-6-yl-hexanoic acid methyl ester)

In a similar way, the named compound is obtained from the corresponding 1,3-phenylene analog.

Yield 69% of the theoretical, of a colorless oil.
NMR (CDCl₃)δ=0.98 (s, 12H); 1.07-1.88 (m, 22H); 2.20 (s, 4H); 3.65 (s, 6H).

EXAMPLE 32

(a) 1,4-cyclohexylidene-bis-(3,3-dimethyl-6-yl-hexanoic acid)

The named compound is obtained by hydrolysis of the methyl ester (example 31(a) in analogy to example 30(a).

Yield 76% of the theoretical; melting point 167°-169° C. (ethyl acetate).
NMR (DDMSO): δ=0.94 (s, 12H); 1.06-1.76 (m, 22H); 2.07 (s, 4H).

(b) 1,3-cyclohexylidene-bis-(3,3-dimethyl-6-yl-hexanoic acid)

Similarly this compound is obtained from the compound of example 31(b).

Yield 89% of the theoretical; melting point 74°-76° C. (ethyl acetate).
NMR (DDMSO): δ=0.94 (s, 12H); 1.06-1.76 (m, 22H); 2.06 (s, 4H).

EXAMPLE 33

1,4-phenylene-bis-(3,3-dimethyl-7-yl-5-heptenoic acid)

(a) 1,4-phenylene-bis-(ethyltriphenyl-phosphonium bromide)

A mixture consisting of 5.84 g (20.0 mmol), 1,4-bis-2-(bromethyl)-benzene and 13.1 g (50.0 mmol) triphenyl phosphine is heated under N₂-atmosphere for 15 mins. to 220° C., and then for 30 mins. at 250° C. The solidified crude product obtained on cooling is recrystallized from ethanol: there is obtained 6.6 g (40%) of a colorless crystalline material with a melting point of 262°-263° C.

(b) 1,4-phenylene-bis-(3,3-dimethyl-7-yl-5-heptenoic acid)

21 ml of a 1.2 mol solution of n-butyl-lithium in hexane is added to a stirred suspension of 8.17 g (10.0 mmol) 1,4-phenylene-bis-(ethyltriphenyl phosphonium bromide) in 300 ml anhydrous ether at room temperature under N₂-atmosphere and the mixture is stirred for a 15 min, after which a solution of 2.65 g (20.0 mmol) 3,3-dimethyl-5-oxo-pentanoic acid methyl ester in 10 ml ether is added dropwise and the mixture is then heated subsequently for 2 hours under reflux.

After cooling the precipitate is filtered off, the filtrate is concentrated and the oily residue is taken up in 40 ml 1N KOH and 10 ml ethanol and is heated for 2 hours to 50° C. The volume is then reduced to a half and the mixture is extracted several times with dichloromethane. The aqueous phase is acidified with 2N HCl and extracted several times with dichloromethane. The oil obtained after drying and evaporation of the organic phase is brought to crystallization with ligroin. 1.0 g (26% of the theoretical yield) of a colorless crystalline material with the melting point of 78°-80° C. is obtained.

NMR (DDMSO): δ=0.99 (s, 12H), 2.13 (s, 4H); 2.17 (d,J=7.2 Hz; 4H); 3.33 (d,J=6.9 Hz; 4H); 5.50–5.64 (m, 4H); 7.08 (s, 4H).

EXAMPLE 34

1,3-phenylene-bis-(3,3-dimethyl-7-yl-5-heptenoic acid)

(a) 1,3-phenylene-bis-(ethyltriphenyl phosphonium bromide) is obtained analogously to example 33(a) from 1,3-bis-(2-bromethyl)-benzene and triphenylphosphine.

Yield 42% of the theoretical, colorless crystals; melting point 219°–220° C. (methanol).

(b) 1,3-phenylene-bis-(3,3-dimethyl-7-yl-5-heptenoic acid) is obtained analogously to example 33(b) using 1,3-phenylene-bis-(ethyltriphenyl phosphonium bromide).

Yield: 51% of the theoretical; colorless oil, $n_D^{26}=1.5202$.

Rf=0.55 (DC-lates Merck 60/toluene-dioxanne-acetic acid 90:25:10) or 0.27 (n-heptane-ethyl acetate 1:1).

EXAMPLE 35

(a) 1,4-phenylene-bis-(3,3-dimethyl-7-yl-heptanoic acid) is obtained from 1,4-phenylene-bis-(3,3-dimethyl-7-yl-5-heptenoic acid), example 33, by normal pressure hydration using palladium as the catalyst.

Yield 52% of the theoretical; melting point 117°–119° C.

NMR (CDCl$_3$): δ=1.00 (s, 12H); 1.27–1.47 (m, 12H); 2.20. (s, 4H); 2.47–2.73 (m, 4H), 7.08 (s, 4H).

(b) 1,3-phenylene-bis-(3,3-dimethyl-7-yl-heptanoic acid) is obtained analogously.

Yield 41% of the theoretical; colorless crystals, melting point 63°–64° C.

NMR (CDCl$_3$): δ=1.00 (s, 12H); 1.27–1.80 (m, 12H); 2.22 (s, 4H); 2.43–2.77 (m, 4H); 6.87–7.20 (m, 4H).

EXAMPLE 36

By hydration of the corresponding 1,4-phenylene-bis-acid or the 1,3-phenylene-bis-acid on rhodium contact one obtains in analogy to example 31.

(a) 1,4-cyclohexylidene-bis-(3,3-dimethyl-7-yl-heptanoic acid)

Yield: 72% of the theoretical; colorless oil.
NMR (CDCl$_3$): δ=0.77–1.85 (m, 26H); 1.02 (s, 12H); 2.22 (s, 4H).

(b) 1,3-cyclohylidene-bis-(3,3-dimethyl-7-yl-heptanoic acid)

Yield 66.% of the theoretical
Melting point: 52°–55° C. (water).
NMR (CDCl$_3$): δ=0.80–1.80 (m, 26H); 1.02 (s, 12H); 2.23 (s, 4H).

EXAMPLE 37

1,4-phenylene-bis-(3,3-dimethyl-5-oxo-7-yl-heptanoic acid)

14.6 g (50.0 mmol) 1,4-bis-(2-bromethyl)-benzene in 100 ml anhydrous ether is dropped on to 2.40 g (0.10 g atom) magnesium turnings with stirring, so that the reaction mixture boils. On completion of the addition, the mixture is heated under reflux for 1.5 hours, is cooled and then 10.1 g (55.0 mmol) cadmium chloride are rapidly added. The mixture is again heated under reflux for 45 min, the then distilled off and 100 ml benzene is added to the reaction mixture. The suspension thus obtained is added with vigorous stirring to a solution of 17.3 g (50.0 mmol) 3,3-dimethyl glutaric acid-methyl ester chloride in 25 ml benzene, is heated for 45 min under reflux, cooled and decomposed by the addition of 2N H$_2$SO$_4$. The crude product obtained after separation, drying and reduction of the organic phase is dissolved in 100 ml ethanol and 100 ml 1N KOH and heated for 3 hours at 60° C. Subsequently, the volume is reduced to half, is extracted several times with ether and acidified with 2N HCl. The aqueous phase is then extracted several times with ether, and the combined extracts are dried and evaporated. The residual oil is crystallized in ligroin/ether. 4.1 g (20% of the theoretical) colorless crystals with a melting point of 116°–120° C. (isopropanol).

NMR (CDCl$_3$): δ=1.06 (s, 12H); 2.55 (s, broad; 8H); 2.50–3.00 (m, 8H); 7.03 (s, 4H).

EXAMPLE 38

1,4-phenylene-bis-(3,3-dimethyl-7-yl-heptanoic acid)

A mixture consisting of 1.05 g (2.50 mmol) 1,4-phenylene-bis-(3,3-dimethyl-5-oxo-7-yl-heptanoic acid), example 37, 1.00 g (17.0 mmol) potassium hydroxide and 1.03 g (20.0 mmol) hydrazine hydrate is heated in 10 ml diethylene glycol for 2 hours under reflux, then for 5 hours at 200° C. to distil off the water. Subsequently, the mixture is cooled and poured into 70 ml water and acidified with diluted hydrochloric acid. The mixture is stirred for 1 hour and the precipitate is collected.

0.60 g (61) colorless crystals with a melting point of 118°–120° C. (toluene).

The compound is identical to that obtained according to Example 35(a).

The pharmacological activities of the compounds of formula (I) according to the invention could be demonstrated by means of in-vivo experiments in rats and Psamomys Obesus in accordance with standard methods. Some of these experiments are described hereinafter in detail and illustrated by the diagrams in the attached drawings.

Figure 1B:
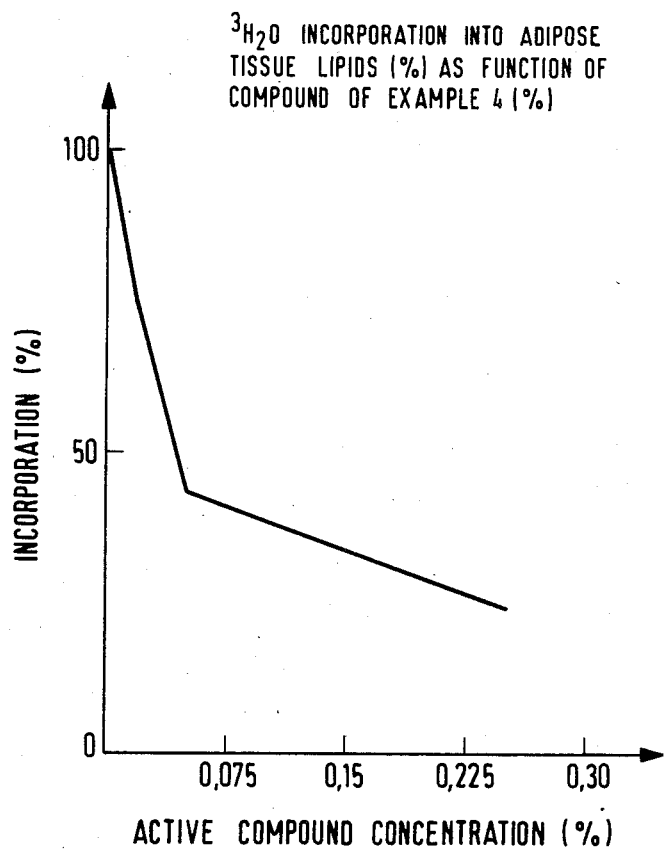

The results are represented in FIGS. 1, 2 and 3 of the attached drawings showing the average tritium incorporation in the test animals as a percentage of the incorporation in the control group (taken as 100%).

Figure 4:
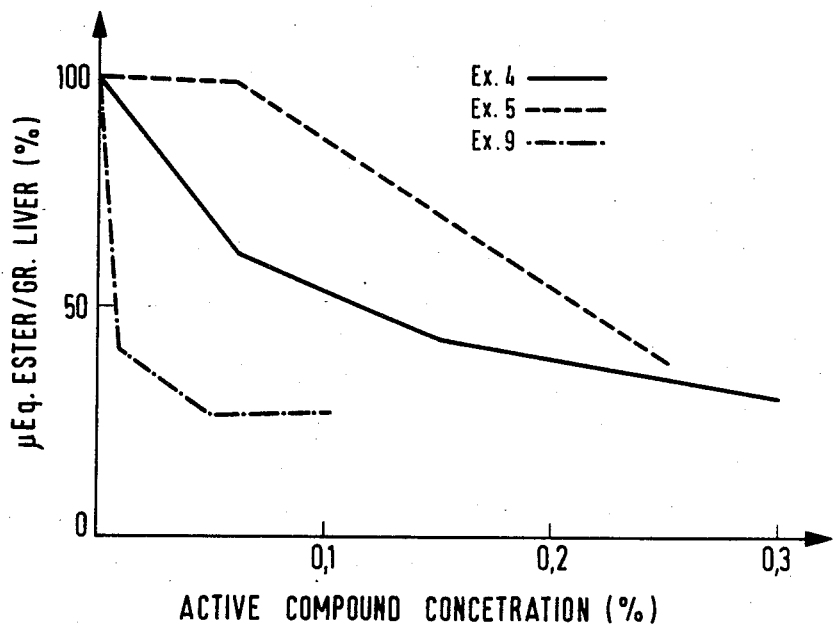

The reduction in liver triglyceride content of rats fed with carbohydrate-rich diet supplemented with compounds of Examples 4, 5 and 9 (as compared to the control group=100%) is shown in FIG. 4 of the attached drawings.

EXPERIMENT I(b)

$^3$H$_2$O incorporation into liver lipids in vico (in μmole/gr liver) was tested in rats fed for 3 days a single daily meal of a high carbohydrate diet containing 0.25% of the active compound of Example 4. The results are shown in the following table I.

TABLE I

| $^3$H$_2$O incorporation into liver total lipid, triglyceride and cholesterol (μmole/gr liver) | | |
|---|---|---|
| Total Lipid | Triglyceride | Cholesterol |
| Non-treated (n = 5)   157 ± 34 | 107 ± 21 | 2.7 ± 1.1 |

TABLE I-continued $^3H_2O$ incorporation into liver total lipid, triglyceride and cholesterol (μmole/gr liver)

|  | Total Lipid | Triglyceride | Cholesterol |
|---|---|---|---|
| Treated (n = 5) | 47 ± 5 | 19 ± 2 | 0.8 ± 0.2 |

EXPERIMENT I(c)

The procedure of Experiment I(b) was repeated for 5 days. The results are shown in the following Table II:

I. EXPERIMENTS IN RATS IN VIVO

Rats that have previously been starved for 48 hours, were meal-fed or fed ad libitum a high carbohydrate, fat-free diet for 3–5 days, the diet being supplemented with the active compounds of formula (I) at dosages of 25–250 mg per Kg body weight per day. The biological effects in-vivo were evaluated by following the rate of incorporation of injected radioactive precursors (mainly $^3H_2O$) into liver and adipose tissue lipids and comparing the results observed with those obtained from groups of non-treated rats ("control groups"). Dose-response curves were plotted.

The hypolipidemic effect was followed by measuring the triglycerides and cholesterol content in serum of treated rats as compared to non-treated rats.

EXPERIMENT I(a)

Incorporation of $^3H_2O$ into neutral fat in liver and adipose tissue and into liver cholesterol in vivo.

$^3H_2O$ incorporation into liver and adipose tissue lipids in vivo was tested in rats fed a high carbohydrate diet ad libitum for three days, supplemented with varying proportions (in percent of the diet) of the active compounds of Examples 4, 5 and 9. $^3H_2O$ was then administered to the animals and the rates of incorporation of tritium (in μmole/gr/60 min) into various lipid fractions in liver and adipose tissue were determined and compared to the tritium incorporation under identical conditions in the control groups of rats.

TABLE II $^3H_2O$ incorporation into liver total lipid, triglyceride and cholesterol (μmole/gr liver)

|  | Total Lipid | Triglyceride | Cholesterol |
|---|---|---|---|
| Non-treated (n = 5) | 107 ± 18 | 71 ± 12 | 2.8 ± 0.8 |
| Treated (n = 5) | 53 ± 13 | 20 ± 7 | 1.4 ± 0.4 |

EXPERIMENT I(d)

Figure 5:
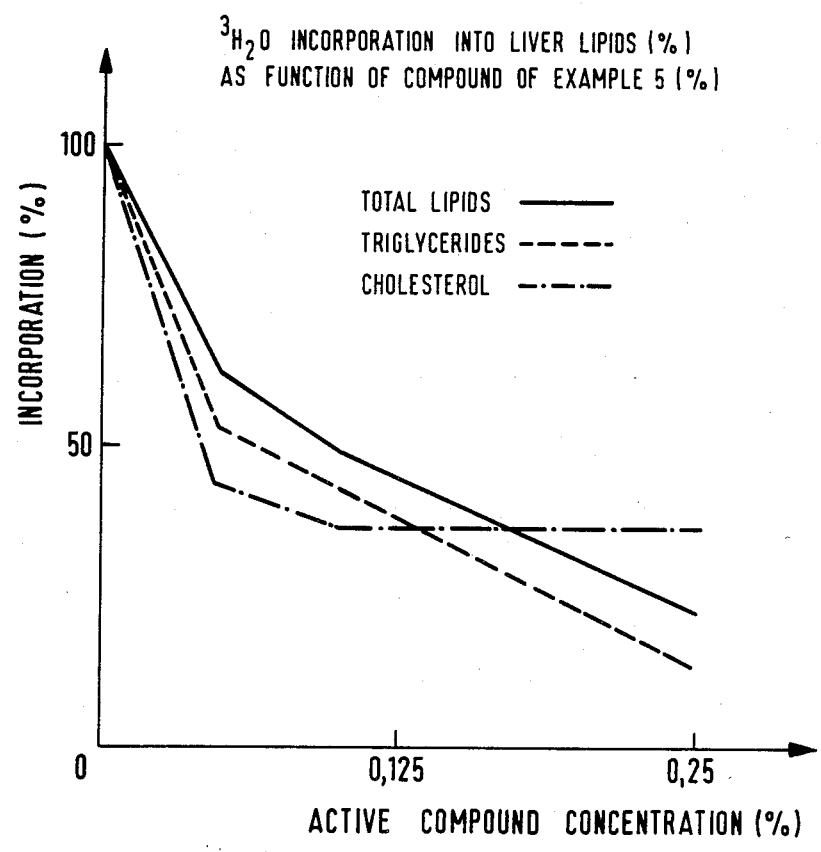

A group of rats were meal-fed once daily for 3 days with a high carbohydrate, fat-free diet containing various percentages of the active compound of Example 5. $^3H_2O$ incorporation into liver lipids (total), triglycerides and cholesterol (as compared to the control group = 100%) are shown in FIG. 5 of the attached drawings.

EXPERIMENT I(e)

Rats starved for 48 hours were fed a high carbohydrate, fat-free diet ad libitum for 3 or 5 days, supplemented with the active compound of Example 4 at the proportions shown in the following Table III. The serum lipids were determined in the treated rats and compared to a non-treated control group.

TABLE III

|  |  | Serum Lipids (mg %) | |
|---|---|---|---|
|  |  | Triglycerides | Cholesterol |
| Active Compound | Non-treated (n = 8) | 41 ± 6 | 64 ± 10 |
|  | 0.06% (n = 5) | 15 ± 4 | 38 ± 5 |
|  | 0.15% (n = 5) | 21 ± 4 | 32 ± 5 |
|  | 0.25% (n = 5) | 15 ± 4 | 31 ± 3 |

EXPERIMENT I(f)

Rats starved for 48 hours were fed a high carbohydrate, fat-free diet supplemented with 0.25% of the active compound of Example 5 for 3 days ad libitum. The observed serum lipids are shown in the following Table IV.

TABLE IV

|  | Serum Lipids (mg %) | |
|---|---|---|
|  | Triglycerides | Cholesterol |
| Non-treated | 48 ± 6 (n = 9) | 80 ± 12 (n = 12) |
| Treated | 33 ± 3 (n = 9) | 40 ± 11 (n = 12) |

The observed serum lipoprotein profile as determined in this experiment is shown in the following Table V.

TABLE V

|  | Non-treated | Treated |
|---|---|---|
| VLDL cholesterol (mg %) | 23.00 | 10.00 |
| LDL cholesterol (mg %) | 19.00 | 6.00 |
| HDL cholesterol (mg %) | 43.00 | 24.00 |
| HDL (VLDL + LDL) | 1.05 | 1.50 |

EXPERIMENT I(g)

The $LD_{50}$ of the active compound of Example 4 in rats was found to be >7 gr/Kg body weight (p.o.).

SUMMARY

The following conclusions were reached with regard to the biological effects of the active compound of Example 4, chosen as a representative active compound:

(a) The active compound was found to block the in vivo incorporation of $^3H_2O$ into neutral fat (diglycerides, triglycerides) in liver (80% inhibition at 250 mg/Kg body wt/day; 50% inhibition at 100 mg/Kg body wt/day), as well as in adipose tissue.

(b) The active compound was found to block the in vivo incorporation of $^3H_2O$ into cholesterol in liver (80% inhibition at 250 mg/Kg body wt/day; 50% inhibition at 100 mg/Kg body wt/day).

(c) Inhibition of neutral fat and cholesterol synthesis in liver exerted by the active compound resulted in an up to 60% decrease in serum glycerides and a 50% decrease in serum cholesterol, as well as a significant change in the serum lipoprotein profile.

(d) Inhibition of neutral fat synthesis in liver exerted by the active compound resulted in 30–50% decrease in the triglyceride content of the liver.

(e) It has been shown by a series of additional experiments on rats that the active compound does not affect the oxidation of glucose, palmitate or acetate to $CO_2$ in vivo.

II. EXPERIMENTS WITH PSAMOMYS OBESUS

Psamomys Obesus were fed "Amrod 935" Purina Chow diet supplemented with 0.1% of the active compound of Example 4, ad libitum, for periods of 80 or 140 days. The biological effects of the active compound in vivo were evaluated as reported in the following experiments.

EXPERIMENT II(a)

Groups of young and old Psamomys were fed the above described diet for 140 and 80 days, respectively, whereafter the serum triglyceride and cholesterol levels were determined. The results are shown in the following Table VI.

TABLE VI

|  | Serum Lipids (mg %) | |
|---|---|---|
|  | Triglycerides | Cholesterol |
| Young animals: |  |  |
| Non-treated (n = 5) | 205 ± 29 | 65 ± 7 |
| Treated (n = 7) for 140 days | 62 ± 15 | 46 ± 7 |
| Old animals: |  |  |
| Non-treated (n = 5) | 220 ± 48 | 146 ± 6 |
| Treated (n = 5) for 80 days | 77 ± 35 | 92 ± 6 |

EXPERIMENT II(b)

The above experiment was repeated with groups of young and old Psamomys and the body weight determined. The results are shown in the following Table VII.

TABLE VII

|  | Non-treated (n = 5) | Treated (n = 7) |
|---|---|---|
| Young animals |  |  |
| Initial weight (gr) average | 100 ± 11 | 92 ± 19 |
| Weight gain (gr) average | 57 ± 33 | 36 ± 12 |
| Weight gain (gr) | 38, 38, 40, 55, 116 | 25, 29, 31, 32, 33, 38, 62 |
| Siblings' weight grain (gr) |  |  |
| a. | 55 | 25, 33 |
| b. | 116 | 31, 38 |
| Old animals |  |  |
| Initial weight (gr) average | 246 ± 26 | 254 ± 52 |
| Weight gain (gr) average | 11 ± 13 | −26 ± 8 |

EXPERIMENT II(c)

Figure 6:
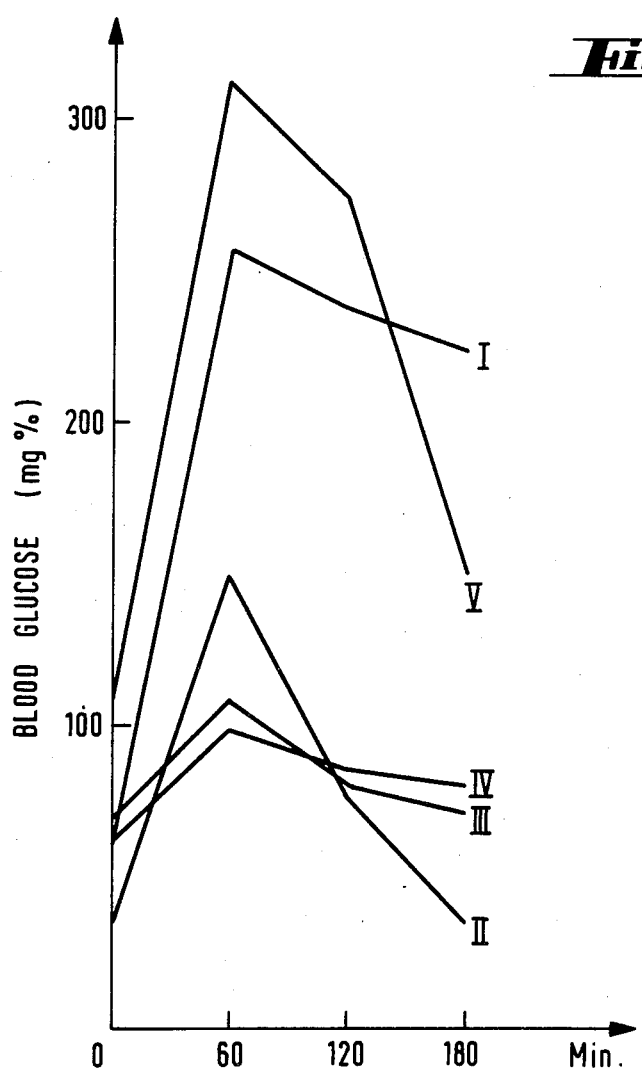

Six Psamomys Obesus fed Purina Chow diet ad libitum were selected for their diabetic trait by following their glucose tolerance test (GTT). The selected animals were then treated by feeding the same Purina diet supplemented with 0.1% of the active compound of Example 4 for periods varying between 30-70 days. The GTT was followed periodically throughout this period, as well as for 50 more days after the drug-supplemented diet had been replaced with the normal diet. A diagram of the GTT curves obtained with one representative animal is shown in FIG. 6 of the attached drawings. The GTT values for all six animals are shown in the following Table VIII as the sum of the glucose values observed at $0^h$, $1^h$, $2^h$, $3^h$.

TABLE VIII

GLUCOSE TOLERANCE TEST
SUM OF GLUCOSE VALUES AT 0, 1, 2, $3^h$.

| Psamomys | Pretreatment | Treatment | Elimination of Treatment |
|---|---|---|---|
| I | 779, 1082 | 364 |  |
| II | 947, 980, 958 | 442 |  |
| III | 790 | 296, 329, 326 | 849 |
| IV | 992 | 358, 336, 465 | 1049 |
| V | 867 | 434, 257, 388 | 470 |

TABLE VIII-continued

GLUCOSE TOLERANCE TEST
SUM OF GLUCOSE VALUES AT 0, 1, 2, $3^h$.

| Psamomys | Pretreatment | Treatment | Elimination of Treatment |
|---|---|---|---|
| VI | 717 | 555, 555, |  |

These results show that administration of the active compound of Example 4 resulted in correction of the GTT curve in 5 or 6 test animals, and that after termination of the treatment, the animals were found to revert to their original diabetic trait. Moreover, the serum insulin levels during the treatment period were found to be lower than 40 uu/ml, as compared to 40-200 uu/ml in the non-treated diabetic animals.

It is of interest to note that the active compound of Example 4 affects neither diabetes induced by steptozocin in rats, nor the GT of non-diabetic Psamomys.

It is to be understood that the present invention is not limited to the embodiments disclosed which are illustratively offered and that modifications may be made without departing from the invention.

I claim:

1. A pharmaceutical composition comprising, as active ingredient, at least one pharmaceutically acceptable compound of the general formula

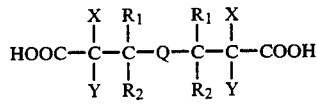

or an in-vivo hydrolyzable functional derivative selected from the group consisting of salts with pharmaceutically acceptable inorganic or organic cations; esters; amides; and anhydrides with lower alkanoic acids; wherein $R_1$ and $R_2$ each independently represents an hydrocarbyl selected from the group consisting of lower alkyl; alkenyl; alkynyl; or cycloalkyl;

X and Y each independently represents hydrogen, lower alkyl, halogen, cyano, carboxy, lower alkoxycarbonyl and carbamoyl; and Q represents alkylene of 8 to 14 carbon atoms, wherein 1 or 2 carbon atoms are optionally replaced with O, S or N (lower alkyl);

together with a solid or liquid pharmaceutically acceptable carrier, diluent or excipient.

2. A pharmaceutical composition according to claim 1, in which $R_1$ and $R_2$ are each lower alkyl, Y is hydrogen and Q is a straight polymethylene chain of 8-14 carbons.

3. A pharmaceutical composition according to claim 1, wherein said pharmaceutically acceptable compound is of the formula

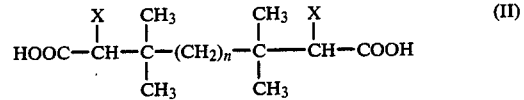

wherein X is hydrogen, lower alkyl, fluoro, chloro, bromo or cyano; and n is an integer of 8-14.

4. A pharmaceutical composition according to claim 1, wherein said pharmaceutically acceptable compound is a said in-vivo hydrolyzable functional derivative selected from the group consisting of salts with pharmaceutically acceptable inorganic or organic cations, esters, amides and anhydrides with lower alkanoic acid.

5. A pharmaceutical composition comprising, together with a solid or liquid pharmaceutically acceptable carrier, diluent or excipient, at least one pharmaceutically acceptable compound selected from the group consisting of:

3,3,14,14-tetramethyl-hexadecane-1,16-dioic acid;
3,3,16,16-tetramethyl-octadecane-1,18-dioic acid;
3,3,12,12-tetramethyl-tetradeca-1,14-dioic acid;
2,15-dicyano-3,3,,14,14-tetramethyl-hexadecane-1,16-dioic acid;
2,15-dibromo-3,3,14,14-tetramethyl-hexadecane-1,16-dioic acid;
2,3,3,14,14,15-hexamethyl-hexadecane-1,16-dioic acid;
1,14-diethoxycarbonyl-2,2,13,13-tetramethyl-tetradecane;
1,14-di(ethoxycarbonyl)-1,14-dibromo-2,2,13,13-tetramethyl-tetradecane;
1,14-bis-carbamoyl-2,2,13,13-tetramethyl-tetradecane;
1,1,14,14-tetra(ethoxycarbonyl)-2,2,13,13-tetramethyl-tetradecane;
1,1,16,16-tetra(ethoxycarbonyl)-2,2,15,15-tetramethyl-hexadecane;
1,1,12,12-tetra(ethoxycarbonyl)-2,2,11,11-tetramethyl-dodecane; and
1,14-di-(ethoxycarbonyl)-1,14-dicyano-2,2,13,13-tetramethyl-tetradecane.

6. A pharmaceutical composition according to claim 1 in a form adapted for oral administration.

7. A pharmaceutical composition according to claim 1 in a form adapted for parenteral administration.

8. A pharmaceutical composition according to claim 1 in unit dosage form.

9. A pharmaceutical composition according to claim 1 comprising 50–500 mg of said pharmaceutically acceptable compound.

10. A pharmaceutical composition according to claim 1 wherein at least one of X or Y is cyano.

11. A pharmaceutical composition according to claim 1 wherein at least on of X and Y is halogen.

12. A pharmaceutical composition according to claim 11, wherein one of X and Y is halogen and the other of X and Y is halogen or hydrogen.

13. A pharmaceutical composition according to claim 12, wherein $R_1$ and $R_2$ are lower alkyl.

14. A pharmaceutical composition according to claim 13 wherein $R_1$ and $R_2$ are methyl.

15. A pharmaceutical composition according to claim 14 wherein Q is linear alkylene.

16. A method of reducing serum cholesterol in a patient in need of said therapy without adversely affecting energy metabolism, and which is thus useful in the treatment of obesity, hyperlipidemia and maturity-onset diabetes, comprising
administering to said patient in need of said therapy, an amount sufficient to reduce serum cholesterol levels of a composition in accordance with claim 1.

17. A method according to claim 16 wherein Q is a linear alkylene chain.

18. A method for reducing serum cholesterol in a patient in need of said therapy without adversely affecting energy metabolism, and which is thus useful in the treatment of obesity, hyperlipidemia and maturity-onset diabetes, comprising
administering to said patient in need of said therapy, an amount sufficient to reduce serum cholesterol levels of a composition in accordance with claim 14.

19. A method for reducing serum cholesterol in a patient in need of said therapy without adversely affecting energy metabolism, and which is thus useful in the treatment of obesity, hyperlipidemia and maturity-onset diabetes, comprising
administering to said patient in need of said therapy, an amount sufficient to reduce serum cholesterol levels of a composition in accordance with claim 5.

* * * * *